(12) United States Patent
Lau et al.

(10) Patent No.: US 6,177,099 B1
(45) Date of Patent: *Jan. 23, 2001

(54) MASKING OF LIPOSOMES FROM RES RECOGNITION

(75) Inventors: John R. Lau, Howard; W. Blair Geho, Wooster, both of OH (US)

(73) Assignee: SDG, Inc., Cleveland, OH (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/922,799

(22) Filed: Sep. 3, 1997

Related U.S. Application Data (63) Continuation of application No. 08/640,204, filed on Apr. 30, 1996, now abandoned, which is a continuation of application No. 08/008,779, filed on Jan. 15, 1995, now abandoned, which is a continuation-in-part of application No07/739,485, filed on Aug. 2, 1991, now abandoned. .

(51) Int. Cl.[7] .................................................. A61K 9/127
(52) U.S. Cl. ........................ 424/450; 428/402.2; 436/829
(58) Field of Search ................... 424/450, 1.21, 424/9.321, 95.1, 417, 94.3; 428/402.2; 431/829; 935/54

(56) References Cited

U.S. PATENT DOCUMENTS

| | | | |
|---|---|---|---|
| 4,861,597 | * | 8/1989 | Kida et al. ........................ 424/85.9 |
| 5,169,635 | * | 12/1992 | Ono et al. ........................... 436/829 |
| 5,567,432 | * | 10/1996 | Lau ..................................... 424/450 |

* cited by examiner

Primary Examiner—Gollamudi S. Kishore
(74) Attorney, Agent, or Firm—Heller Ehrman White & McAuliffe LLP (57) ABSTRACT

A biochemical membrane encapsulated by neuraminic acid residue to mask the surface of the membrane from recognition and removal by the scavenging RES cells of the body.

4 Claims, 9 Drawing Sheets

5-amino-3,5-dideoxy-D-glycero-D-galacto-2-methoxy-nonulopyranose-1-onic acid

5-amino-3,5-dideoxy-D-glycero-D-galacto-2-
methoxy-nonulopyranose-1-onic acid

FIG. 5

2-iminothiolane
(Traut's Reagent)

β-methoxy neuraminic
acid 2-iminothiolane
-methoxyneuraminic
acid conjugate

MASKING OF LIPOSOMES FROM RES RECOGNITION

This is a continuation of application Ser. No. 08/640,204, filed Apr. 30, 1996, now abandoned which, in turn, is a continuation of application Ser. No. 08/008/779, filed Jan. 15, 1995, now abandoned which, in turn, is a continuation in part of application Ser. No. 07/739,485 filed on Aug. 2, 1991 now abandoned.

BACKGROUND OF THE INVENTION

SIALIC ACID: An N-acyl derivative of neuraminic acid.

NEURAMINIC ACID: A synthetically-derived sialic acid. The Chemical Abstracts Index names for this molecule are: D-glycero-D-galacto-2-Nonulopyranosidonic acid, methyl 5-amino-3, 5-dideoxy-(9C1); or D-glycero-D-galacto-Nonulopyranosidonic acid, methyl 5-amino-3, 5-dideoxy-(8Cl). Another name for this molecule is Methoxyneuraminic Acid, or Beta-Methoxy Neuraminic Acid. As ordered by the applicant form Sigma Chemical Company, P.O. Box 14508, St. Louis, Mo. 63178, it is named Neuraminic Acid Beta-Methyl-Glycoside (pfs), product number N 5380 (1992 Catalog).

NEURAMINIDASE: An enzyme of the hydrolase class that is in blood and which catalyzes the hydrolysis of glucosidic linkages between a sialic acid residue and a hexose or hexosamine residue at the non-reducing terminal of oligosaccharides in glycoproteins, glycolipids and proteoglycans.

LIPOSOME: A spherical particle in an aqueous medium, formed by a lipid bilayer enclosing an aqueous compartment.

BACKGROUND OF THE INVENTION

Liposomes, also known as vesicles, have been designed to encapsulate a cargo of pharmacological agents useful for in vivo purposes such as the diagnosis and treatment of various diseases and conditions. These cargo-carrying liposomes have, experimentally, shown potential for being site-specific carrier systems for a variety of such agents. Agents so delivered to designated sites in vivo demonstrate significantly enhanced therapeutic indices. Concurrently, decrease in unwanted side effects and wasted portions of dosages is achieved. Agents not so couried spread to nonspecific and often undesirable areas of the body, and possibly cause side effects.

The advantages of the prior art in vivo carrier system have been offset, however, by the deleterious effects of the body's reticuloendothelial system (the "RES"), mainly the liver and spleen. The RES acts to screen the body's circulation. The RES will gradually scavenge from the circulation all material it considers foreign and unwanted. Liposomes have certain physical characteristics which render them susceptible to removal by the RES. Once recognized, liposomes, whether given a site-specific molecule for so-called "targeted" delivery or not, are quickly phagocytosed by the RES along with their cargo. This prior revolutionary carrier system has, until the present invention, and the processor invention of U.S. Pat. No. 4,501,728, remained hampered by the RES, the body's own defense mechanism.

In said earlier invention, U.S. Pat. No. 4,501,728, the sialic acid mechanism for RES avoidance was a system consisting essentially of a biochemical membrane having sialic acid residues that mask the surface membrane from recognition by the RES cells.

Despite the successful application of sialic acid residues to the liposome carrier system, liposomes so disguised from the RES were nevertheless eventually subject to enzymatic action of endogenous neuraminidase in the blood. Specifically, it was found that neuraminidase cleaves the chemical bond between sialic acid and its attached sugar (galactose), thereby allowing the galactose (sugar) on the surface of the liposome to be recognized by the RES's Ashwell receptor of the liver.

Enzymatic removal of the sialic acid is time-dependent. Liposomes intended to circulate for longer periods of time in the vascular system or until attracted to a binding-site, are removed by the RES once the sialic acid mask is compromised or lost.

Along with finding a means to mask the liposome from the RES, it is generally an objective in the art of drug delivery to discover an appropriate site-specific binding molecule. Once discovered, the binding molecule can be incorporated into the liposome. Such masked liposome with its binding molecule, when introduced in vivo, will evade the RES and will carry a designated cargo to a predetermined binding site in the body. When delivered, the cargo is then released to perform its designated function.

SUMMARY OF THE INVENTION

This invention is embodied by the product of a procedure of applying to the external surface of a liposome carrier system, two types of substituent molecules. One such molecule masks the liposome from the RES and is sel ected from the class consisting of those chemicals which are classed biologically as synthetically-derived molecules that prevent phagocytosis by the body's RES and which cannot be degenerated and separated from the liposome by the action of circulating endogenous enzymes.

The other molecule is one which binds to or is bound by a specific site in the body and which is incorporated as part of the liposome carrier. The combined result of the liposome carrier with these two types of substituent molecules, is highly effective delivery of the liposome's therapeutic or diagnostic cargo to a specific body site, having evaded the body's RES.

It is an object of this invention to create a composition of matter for in vivo administration of therapeutic or diagnostic agents, comprising a lipid membrane structure in the form of a liposome or vesicle, a second component which is a synthetically derived molecule that prevents recognition of the liposome or vesicle by the RES and which cannot be cleaved from the liposome or vesicle by the action of endogenous enzymes, and a third component which is a molecule that binds the liposome or vesicle to a specific site in the body and which can be present for site-specific delivery or absent for non-specific delivery of the therapeutic or diagnostic agents in vivo.

This invention is the discovery that superior site specific delivery of the liposome's cargo is obtained by the combined effect of using synthetically-derived RES-avoidance molecules that cannot be cleaved by circulating endogenous enzymes, with site-specific binding molecules that find or are found by a receptor at a desired site in the body.

This invention is also the discovery that superior systemic circulation of liposomes without site-specific delivery, can be achieved using the aforementioned synthetic masking molecules without the site-binding molecule component.

DETAILED DESCRIPTION OF THE PREFERRED EMBODIMENT

This invention embodies a liposomal delivery system consisting essentially of a phospholipid membrane known commonly as vesicles, or liposomes (vesicles and liposomes, as used herein, mean the same thing), with two types of substituent molecules incorporated in the membrane.

One such type of molecule is classed biologically as a synthetic molecule which masks the liposome from the body's RES and which cannot be cleaved from the liposome by circulating endogenous enzymes. The other type of molecule is one which binds to a specific site in the body. The combination allows delivery of a greatly enhanced index of therapeutic or diagnostic cargo to such specific body site.

In the alternative, for superior circulatory life of liposomes without site-specific delivery, the aforementioned site-specific binding molecule can be omitted. B-methoxyneuraminic acid, used herein as a synthetic liposome masking molecule, is used in this description as an example and is preferred because its use is consistent with data shown herein.

The first example set forth hereinafter, is a liposome with a permeable membrane, which is designed and synthesized to circulate in the blood for an extended per$od of time as a non-binding time-release drug delivery system.

The second example set forth hereinafter, is a liposome which, in addition to being masked by the incorporation of neuraminic acid or its biologically active derivatives onto the liposome membrane, is also invested with a site-binding molecule. The inclusion of a site-binding molecule along with the neuraminic acid masking agent, creates a liposome which delivers its cargo to an appropriate specific site of action such as a tumor, without the danger of being removed prematurely from the circulation by the RES.

It has been found, according to this invention, that the combination of masking plus a specific site-binding molecule, such as a monoclonal antibody for binding to tumor cells, produces a quantum step beyond the expected benefits.

Figure 1:
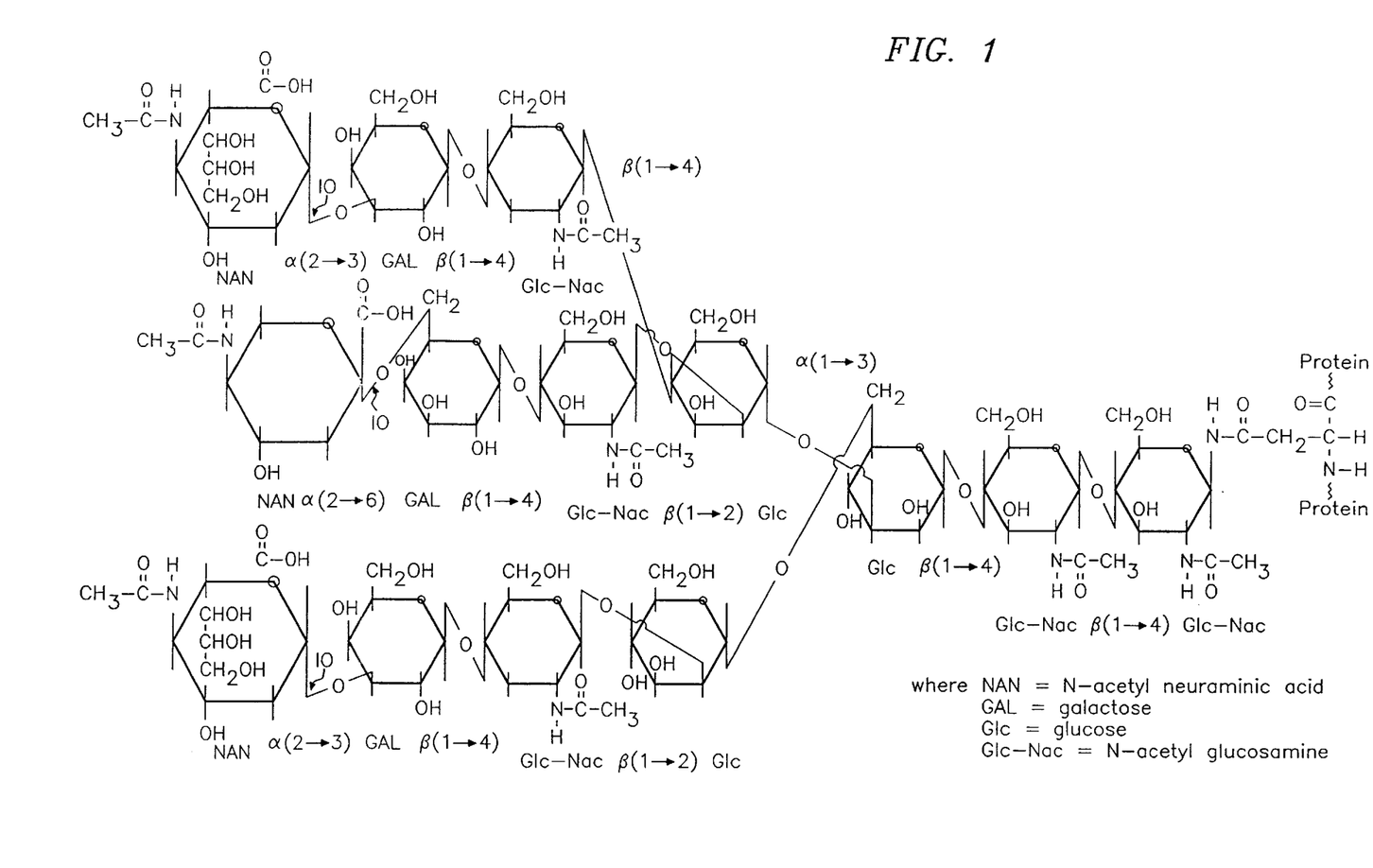
FIG. 1 is a representative of a branched glycoprotein that has sialic acid as the terminal units of the glycan chains.
Figure 1A:
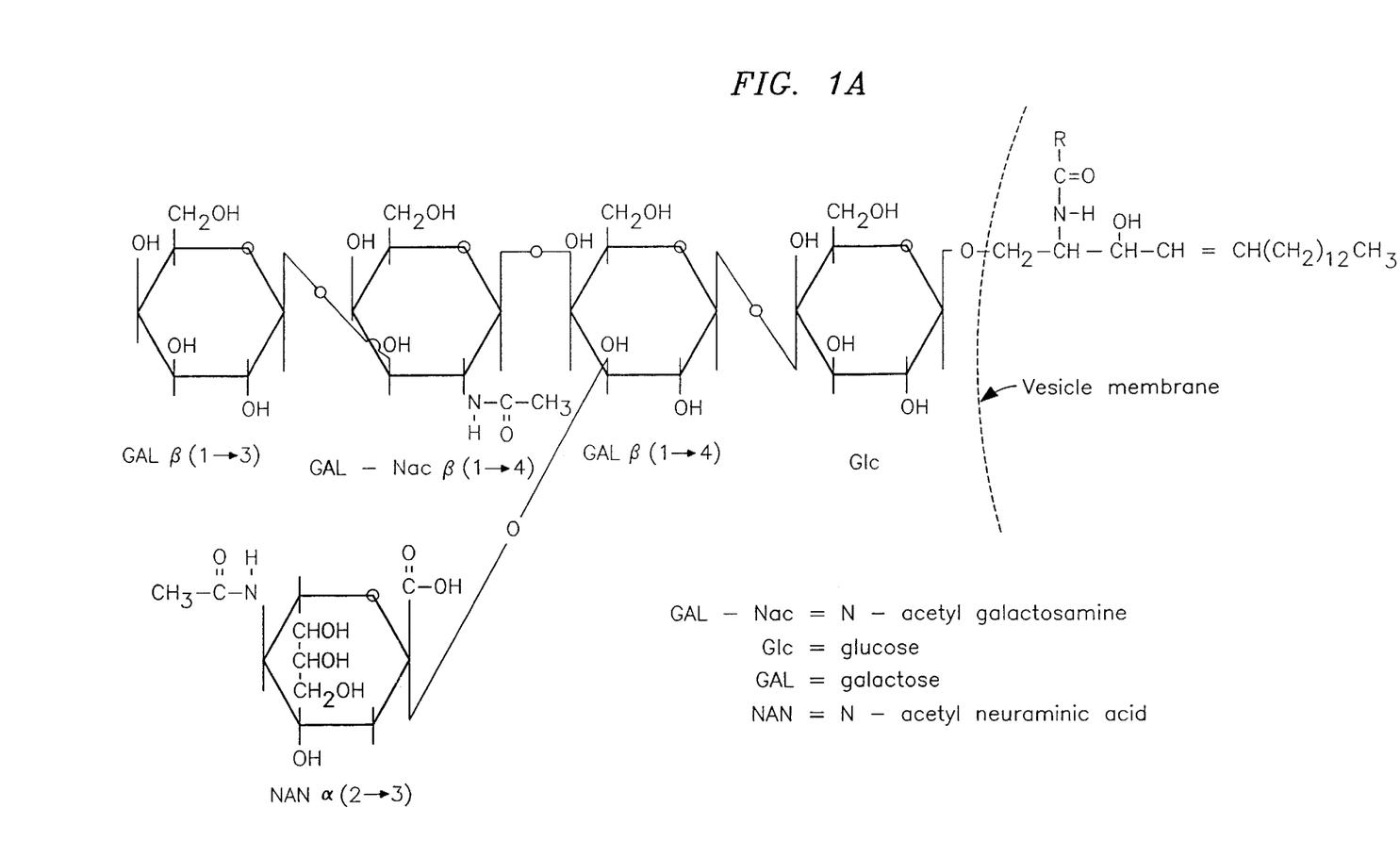

Our former U.S. Pat. No. 4,501,728 teaches and claims a means to use naturally-occurring sialic acid to avoid RES recognition, The structural formula for a glycoprotein with terminal sialic acid units is depicted in FIG. 1. A glycosidic bond connects the sialic acid to the penultimate sugar, usually a galactose.

Use of naturally-occurring sialic acid residues to mask liposomes from the RES enables liposomes to carry therapeutic or diagnostic agents in vivo for extended periods of time. Much like red blood cells, which also have sialic acid residues that perform the same masking function, these liposomes circulate systemically, evading the RES. But like red blood cells, liposomes masked with naturally-occurring sialic acid residues are subject to the action of circulating endogenous enzymes such as neuraminidase, which cleaves the glycosidic bond of the sialic acid, exposing its penultimate sugar to RES recognition. The enzymatic cleavage of this glycosidic bond is by hydrolysis, and occurs at the bond indicated by reference character 10 of FIG. 1.

Despite the fact that RES masking is effectively achieved using naturally-occurring sialic acid residues, it was discovered by the applicants that vastly improved masking-time can be achieved by using a synthetic sialic acid, such as the preferred Beta-methoxyneuramic acid, which cannot be cleaved and thus exposed to the RES by circulating endogenous enzymes. Therefore, the preferred best mode embodiment uses Beta-methoxyneuraminic acid, the systematic name of which is given above in the Definition section. See FIG. 2. Note that the sugar of this molecule has a free primary amino group (—NH—) attached to carbon #5 of the nonulopyranose ring structure, along with a non-reactive B-methoxy group (OCH—) attached to carbon #2 of the ring.

The best mode product of this invention was found to be one in which the following was observed:

1) The bond of this invention is not susceptible to hydrolysis by the enzyme neuraminidase in the plasma of a warm blooded host;
2) The bond is stable both in vivo and in vitro for an indefinite period of time;
3) The bond can be of a secondary amine type;
4) The bond can be of a thio ether type;
6) The bond is not readily hydrolyzable by other circulating endogenous enzymes in the plasma.

Figure 3:
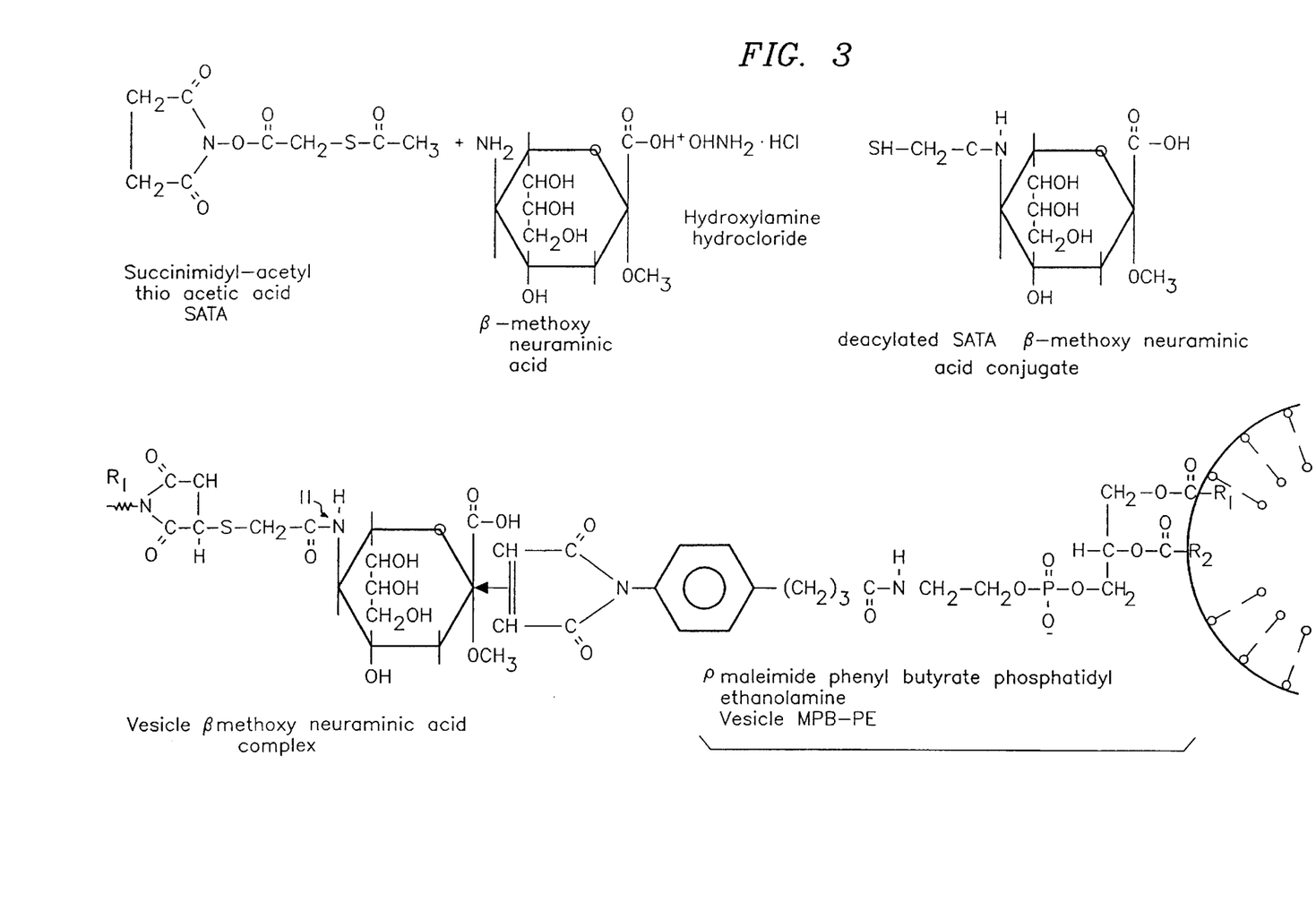
FIG. 3 illustrates the first example of a synthetic pathway by which a non-hydrolyzable secondary amide bond can be created by using an amide linkage to connect the B-methoxyneuraminic acid conjugate to an appropriate bridging molecule.

FIG. 3 illustrates the first example of a synthetic pathway by which a nonhydrolyzable secondary amide bond is created by using an amide linkage to connect the B-methoxyneuraminic acid sugar to an appropriate bridging molecule.

Reference character 11 of FIG. -3 points out the amide linkage (—C—N—) resulting in a secondary amine.

Figure 4:
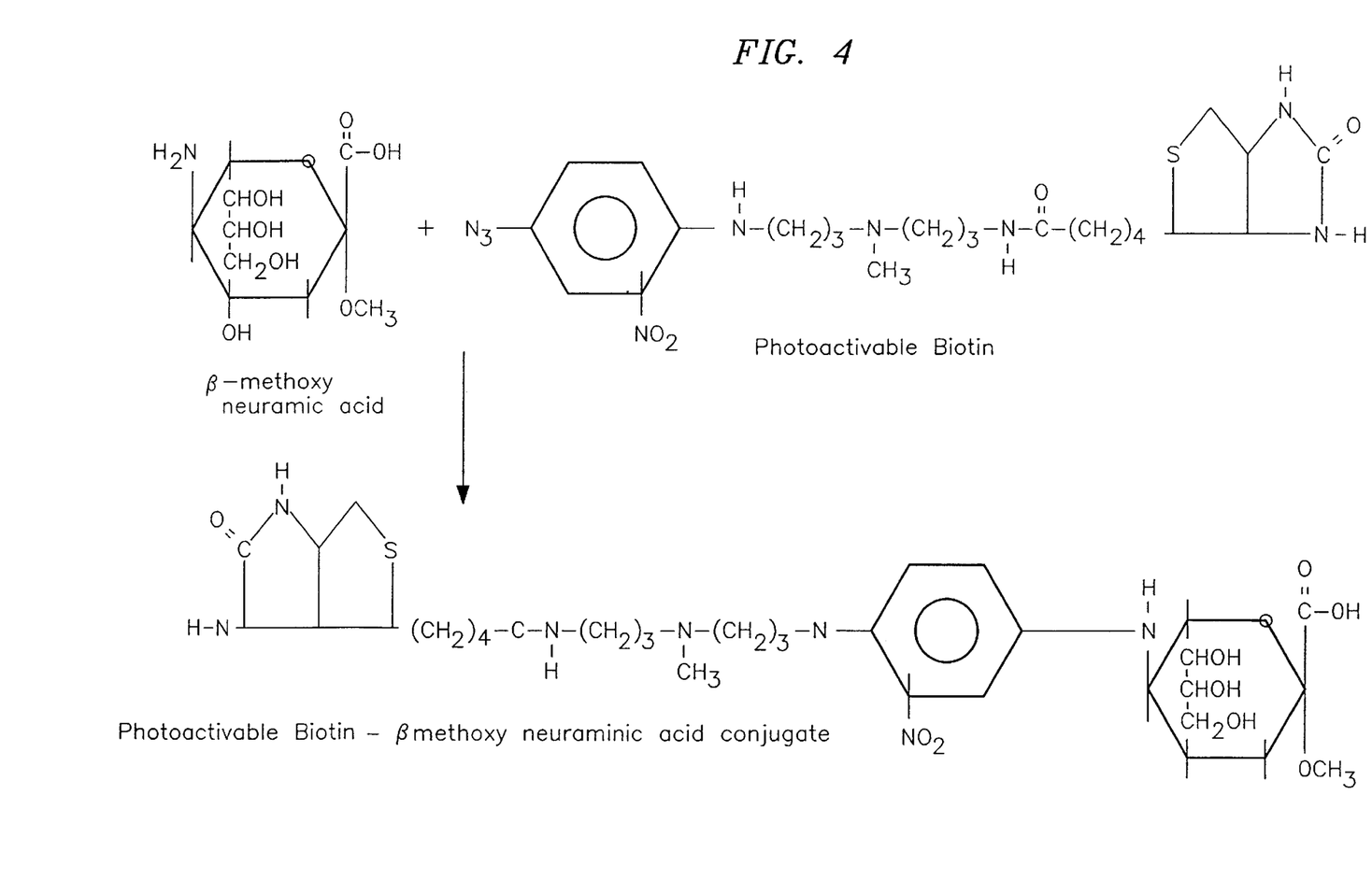
FIG. 4 illustrates another synthetic pathway by which a secondary amide linkage can be formed between B-methoxyneuraminic acid and photoactivatable biotin resulting in a biotin B-methoxyneuraminic acid conjugate that can be attached to a liposome using streptavidin and biotin phosphatidyl ethanol amine.

FIG. 4, illustrates another synthetic pathway by which a secondary amide linkage is formed between B-methoxyneuraminic acid and photoactivatable biotin resulting in a biotin B-methoxyneuraminic acid conjugate that can be attached to 8 liposome using streptavidin and biotin phosphatidyl ethanol amine.

Figure 5:
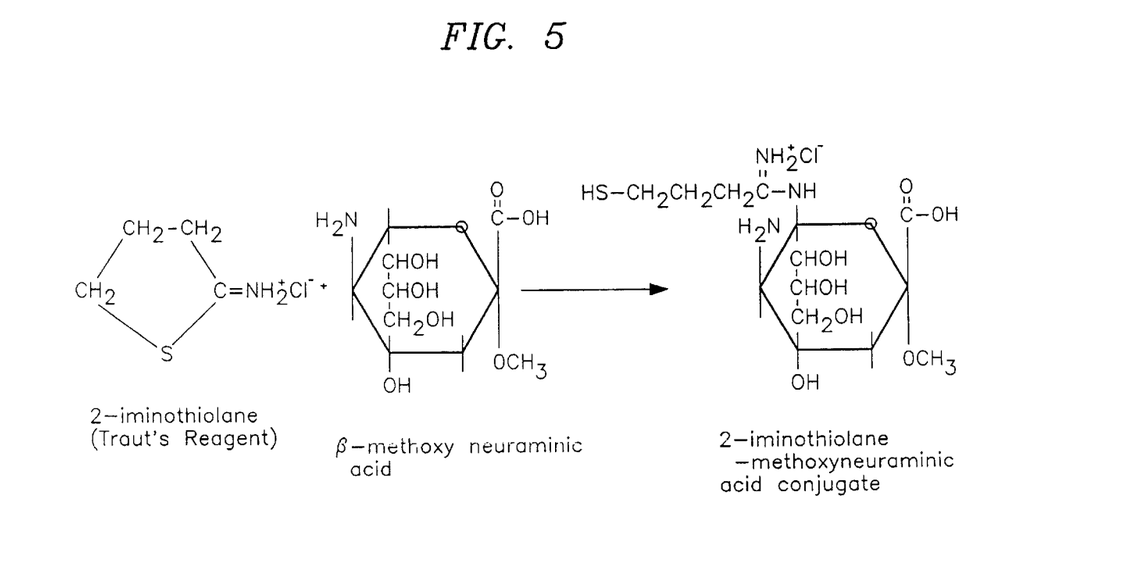
FIG. 5 shows the third type of synthetic pathway which would result in a bond formation between B-methoxyneuraminic acid and 2-iminothiolane (Traut's Reagent), resulting in yet another secondary amine bond that is not hydrolyzable by the circulating endogenous enzyme neuraminidase.

FIG. 5, shows the third type of synthetic pathway resulting in a bond formation between B-methoxyneuraminic acid and 2-iminothiolane (Traut's Reagent) resulting in vet another secondary amine bond that is not hydrolyzable by the circulating endogenous enzyme neuraminidase. While all three examples illustrate the formation of a second amine bond, the —R— group to which the secondary amine is attached is different.

Figure 6A:
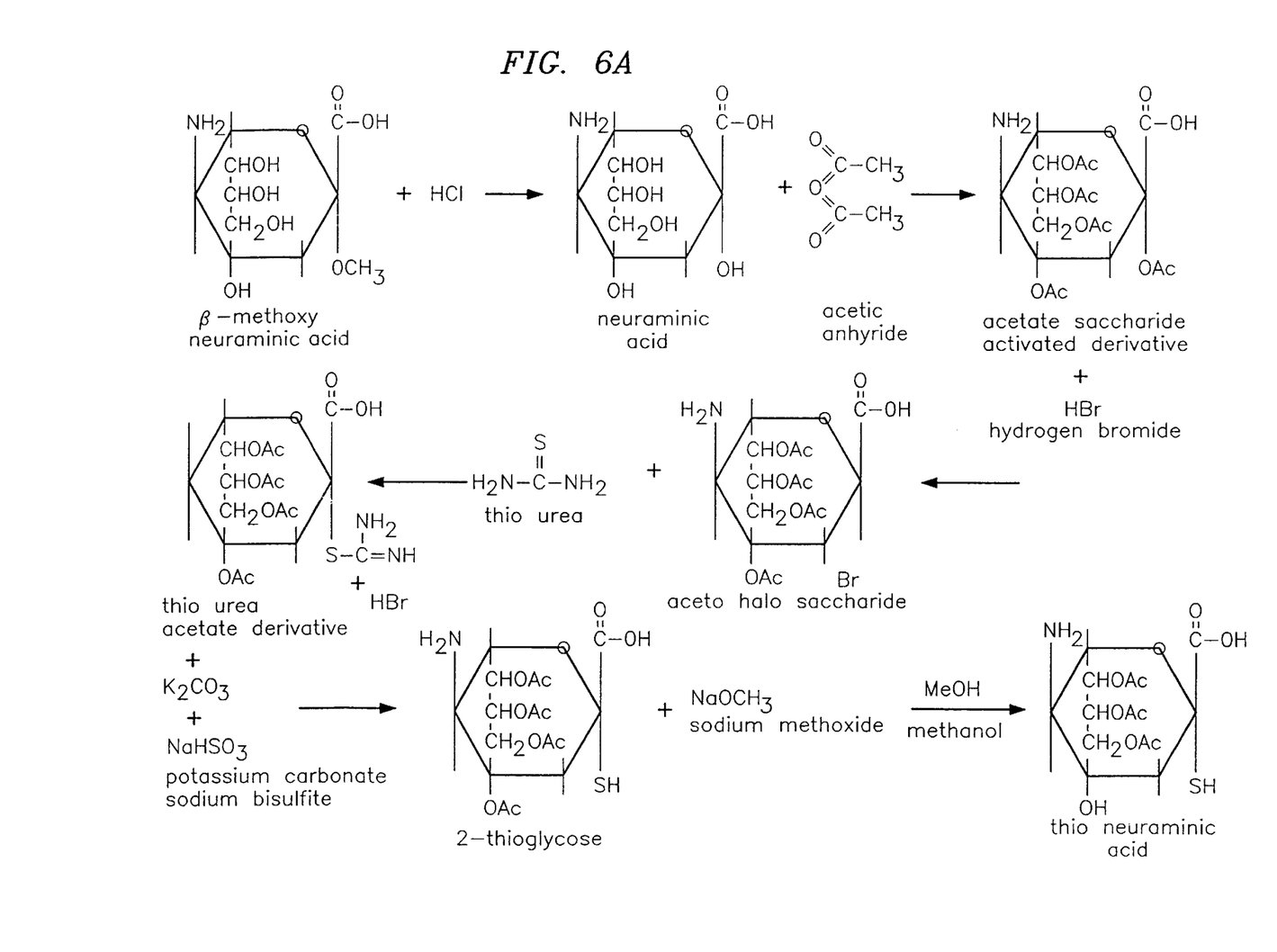
FIGS. 6A and 6B show another synthetic pathway for establishing a non-hydrolyzable bond between neuraminic acid and p-maleimido phenyl butyrate phosphatidyl ethanol amine through the formation of a thio ether bond.
Figure 6B:
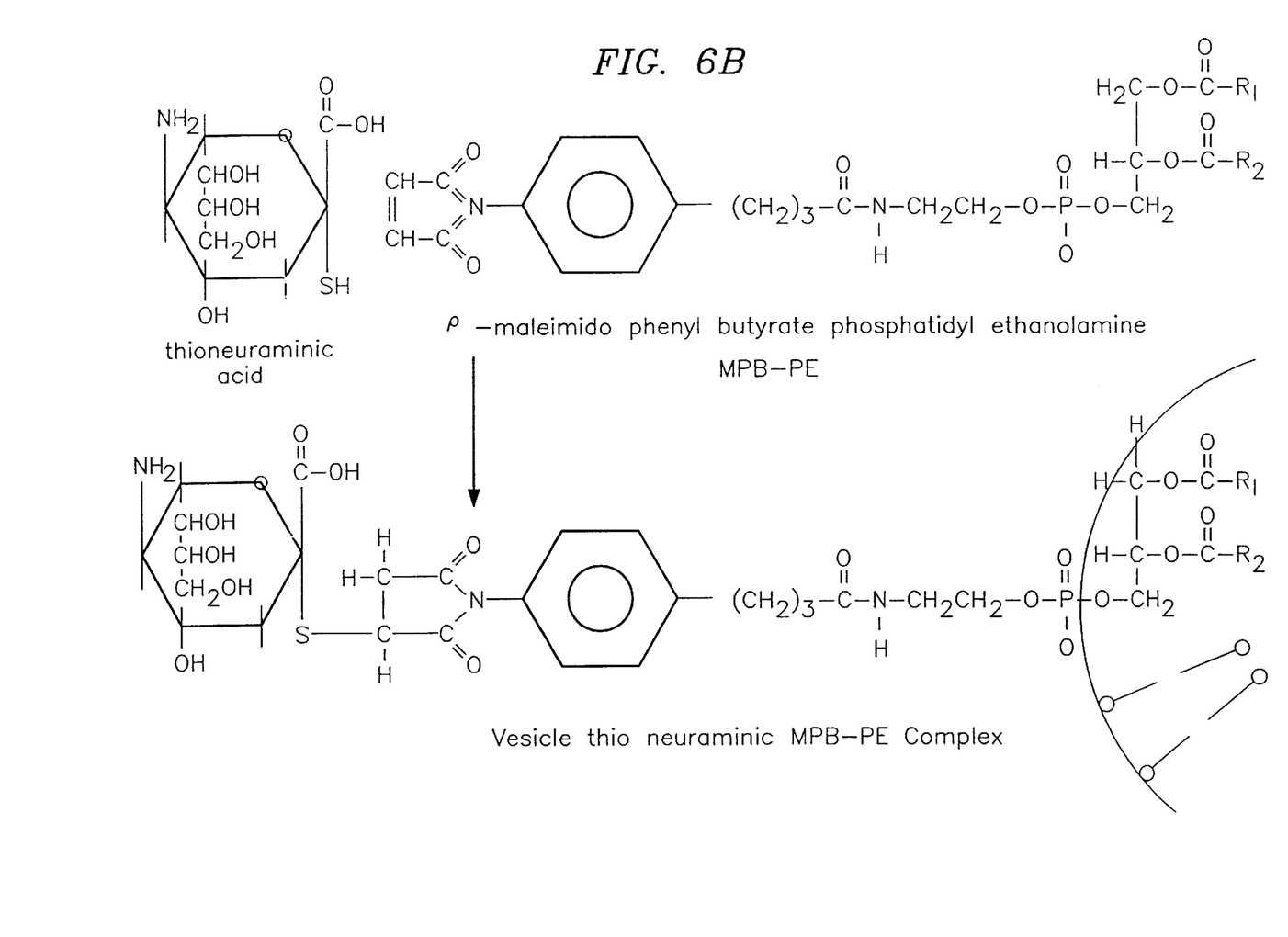

FIG. 6A and FIG. 6B show another synthetic pathway for establishing a non-hydrolyzable bond between neuraminic acid and p-maleimido phenyl butyrate phosphatidyl ethanol amine through the formation of a thio ether bond. In this synthetic pathway, the B-methoxy group is removed from B-methoxyneuraminic acid by HC1. The resulting neuraminic acid is acylated with acetic anhydride to form its fully acylated sugar derivative. This sugar derivative is then reacted with the halo acid hydrogen bromide to form the acetohalo saccharide. The acetohalo saccharide is then reacted with thiourea to form the thiourea acetate derivative, which, in turn, is reacted with potassium carbonate and sodium bisulfite to remove the acetyl groups in order to form the sulfhydryl sugar, 2-thioglycose. 2-thioglycose is reacted with sodium methoxide (a base) in the presence of methanol, to generate the thioneuraminic acid derivative. Since this neuraminic acid sugar has a free sulfhydryl, it reacts with the maleimido group of p-maleimido phenyl butyrate phosphatidyl ethanolamine, which, in turn, is coupled to the vesicle membrane.

By establishing a provision in the aforementioned synthetic pathways for a non-hydrolyzable bond linking the B-methoxyneuraminic acid to the bridging molecule, the circulating half-life of the B-methoxyneuraminic acid-masked liposomes in a warm blooded host is significantly enhanced.

As an example of practicing this invention without using the site-binding molecule, insulin was administered in vivo as the cargo of a porous liposome which had attached to its phospholipid membrane only the synthetic masking molecule B-methoxyneuraminic acid. The liposome was found to circulate in the body for significantly extended periods of time, releasing insulin, because of the fact that the B-methoxyneuraminic acid's sugar group could not be hydrolyzed and separated from the liposome by the endogenous enzyme neuraminidase.

Figure 7:
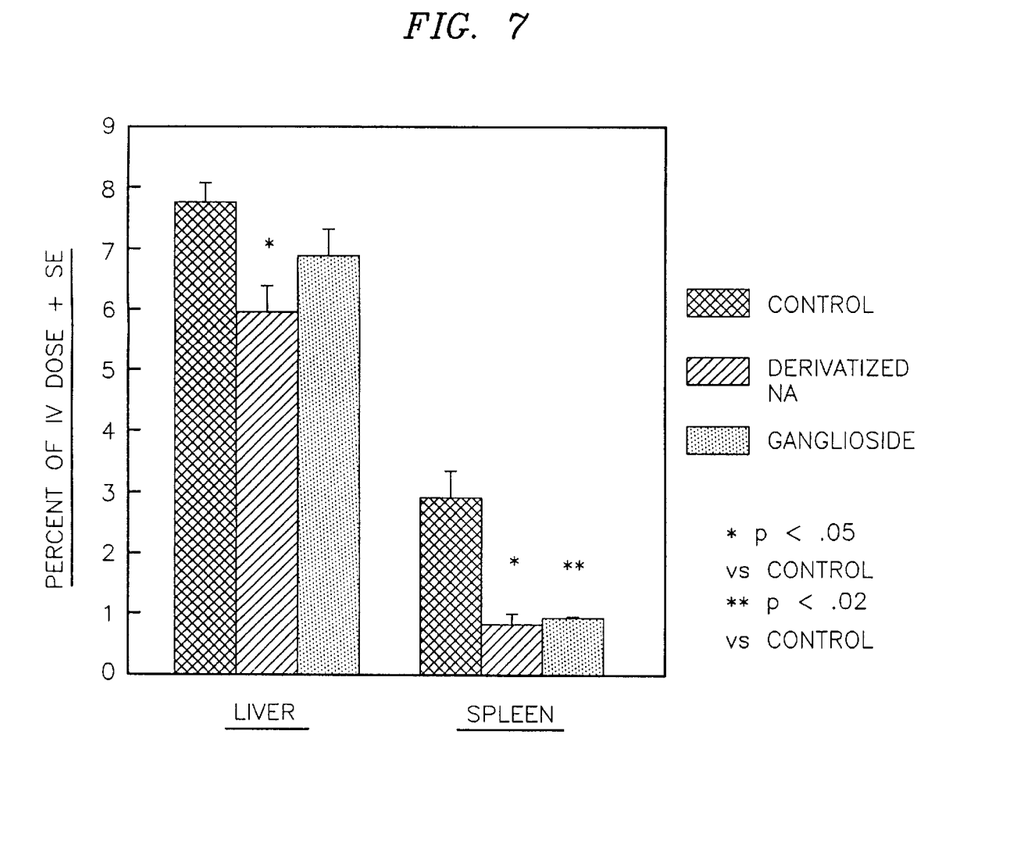
FIG. 7 is a graph showing the 2-hour effect of neuraminic acid on I.V. liposome distribution.
Figure 8:
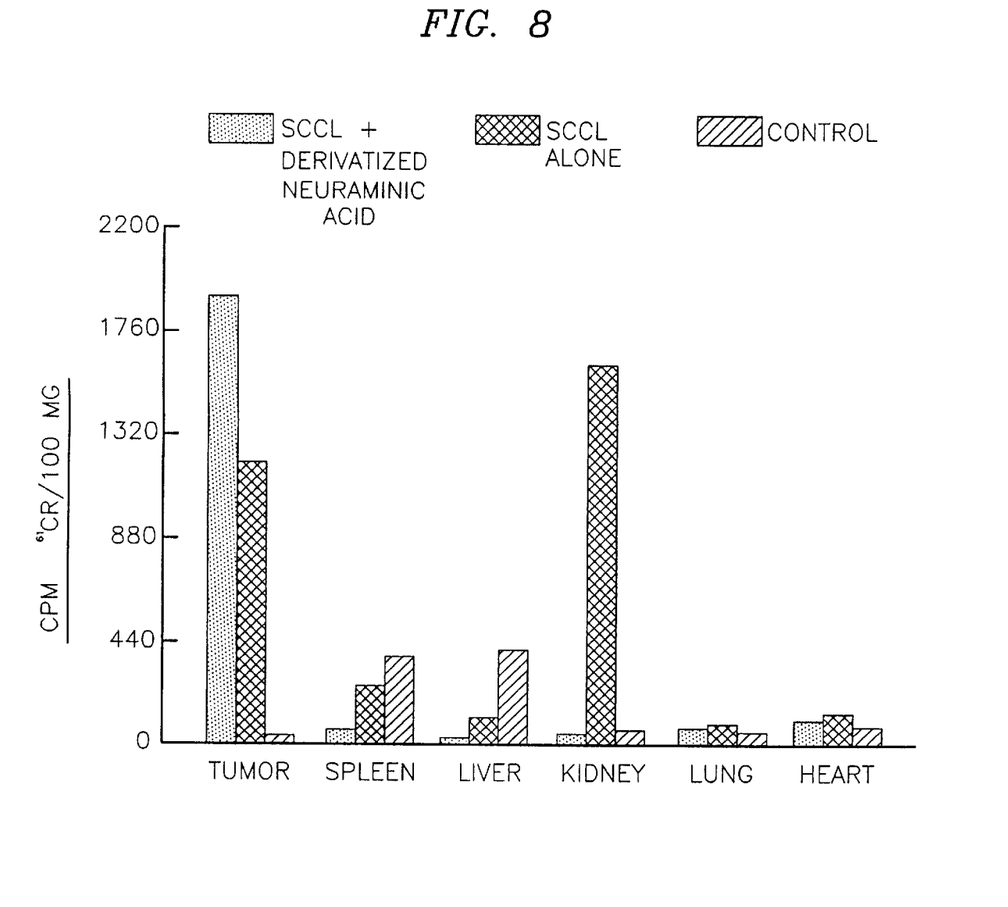
FIG. 8 is a graph showing the effect of neuraminic acid on $^{51}$chromium radiation.

FIGS. 7 and 8, together with the following text, establish the exceptional performance of a liposomal delivery system consisting essentially of a phospholipid membrane with a B-methoxyneuraminic acid substituent, wherein said acid is attached to the liposome by a bond which is not hydrolyzed by a circulating endogenous enzyme such as neuraminidase in the blood of a warm blooded animal.

EXAMPLE #1

AVOIDANCE OF LIVER AND SPLEEN IN RATS

Liposomes were made with the following compositions:

| | DSL | DCP | CHOL | MPB-PE | DERIVA-TIZED NEURA-MINIC ACID | GANGLI-OSIDE |
|---|---|---|---|---|---|---|
| CONTROL (mg) | 42.7 | 9.83 | 3.48 | 0.0 | 0.0 | 0.0 |
| GANGLI-OSIDE (mg) | 42.7 | 9.83 | 3.48 | 0.0 | 0.0 | 0.0 |
| DERIV. N.A. (mg) | 42.7 | 9.83 | 3.48 | 0.0 | 0.6 | 0.0 |

1. DSL = Distearoyl Lecithin
2. DCP = Dicetyl phosphate
3. CHOL = Cholesterol
4. MPB-PE = p-maleimido phenyl butyrate phosphatidyl ethanol The liposomes were made using the method described in U.S. Pat. No. 4,603,044. Briefly, the crusts, having the above compositions, were solubilized with 10.0 ml of 10 mM PhosPhate buffer, PH 7.4, to which a 10 ul aliquot of $^{123}$I-human growth hormone was added. The mixture was sonicated on a Heat Systems Branson Cell Disrupter at setting #4 for 6.0 minutes at 60° C. The sample was then centrifuged for one hour at 20,000 RPM in a Sorvall RC2B centrifuge at 20° C. The supernatant was decanted and 410 ul was chromatographed over a sephadex G-100 column equilibrated with 10 mM phosphate buffer, pH 7.4. The derivatized neuraminic acid (DERIV. N.A.) was then added to the liposomes for the DERIV N.A. sample and allowed to react with the MPB-PE that was already in the liposomal membrane.

These test samples were then tested in normal rats. In the rat study, five rats were used for each group. The test samples were administered intravenously to each rat and the rats' livers and spleens were removed after two hours, under seconal anesthesia, and processed for counting the radiolabel. The results of the study are shown in FIG. 7. The rats that received the liposomes with the synthetically-derived neuraminic acid had significantly fewer liposomes in their livers and spleens than rats receiving the control liposomes without any neuraminic acid. Syntheticallyderived neuraminic acid is B-methoxyneuraminic acid that has been derivatized according to the above specification and does not contain a glycosidic bond that is hydrolyzable by circulating endogenous enzymes, such as neuraminidase.

The rats that received the liposomes with the naturally occurring sialic acid ganglioside showed significantly lower levels of liposomes in their livers than the comparable control rats, but not as low a level of liposomes as was observed in rats receiving the liposomes with the synthetic neuraminic acid derivative. The naturally-occurring ganglioside is a molecule that exhibits a terminal sialic acid residue accompanied by a penultimate galactose group. The sialic acid residue of that ganglioside is connected to a penultimate sugar moiety by a glycosidic bond that is hydrolyzable by the enzyme neuraminidase. The spleens of the rats receiving both the synthetic neuraminic acid and the natural ganglioside were lower than the control rats.

EXAMPLE #2

AVOIDANCE OF LIVER, SPLEEN AND HEART IN NUDE MICE WITH LIPOSOMES TARGETED TO TUMORS

Three types of liposomes were prepared:
Sample A: Tumor specific antibody (SCCL-1); no synthetic neuraminic acid
Sample B: Tumor specific antibody (SCCL-1); with synthetic neuraminic acid
Sample C: Control (non-specific) antibody; no synthetic neuraminic acid Nude mice with xenografted human Small Cell Carcinoma of the Lung (SCCL) were used. Each liposome sample A, B, and C, was subcutaneously injected into the mice. The mice were sacrificed at forty-eight hours and their various tissues were removed for analysis of the radio-label. The data are shown in FIG. 8. It is clearly shown that the most effective binding to the tumor occurred with the liposomes that were both attended to SCCL-1 antibody and were marked from liver and spleen uptake with the synthetic neuraminic acid. The liposomes with the SCCL-1 antibody still did significant targeting to the tumor, but some of the liposomes were found in other tissues. The liposomes that had neither site-binding antibodies of synthetic neuraminic acid were found in significant amounts in liver, spleen, and lung.

A generic representation of naturally-occurring neuraminic acid is shown in FIG. 1.

Five derivatives found naturally in man are:
1. Neu 5 Ac
2. Neu 5,9 $Ac^2$;
3. Neu 5,7,9 $Ac^2$
4. Neu 5 Ac 9 Lt
5. Neu 5 Gc Definitions:
Neu=Neuraminic acid
Ac=acetyl—$CH^3CO$—
Gc=glycolyl=$OHCH^2CO$
Lt=lactyl=$CH^3CHOH)CO$ Neuraminic acid and its above-described derivatives are found naturally in warm-blooded hosts and are known generally as sialic acid and sialic acid derivatives. So-called "GM-1" is a natural sialic acid derivative commonly used for masking liposomes from the RES. Sialic acid itself acts as a protective red blood cell component, to prevent the RES from phagocytosing the red blood cells. The use of sialic acid and its naturally-occurring derivatives for extending the in vivo circulating and binding life of liposomes, however, is limited, because endogenous enzymes circulating in the plasma, such as neuraminidase, cleave the sialic acid or its derivative from the liposome. The unmasked liposomes are then exposed to the RES, and phagocytosed. Red blood cells are likewise phagocytosed when the sialic acid is thus cleaved.

This invention addresses this cleavage problem by using a synthetic sialic acid that forms a non-hydrolyzable bond with the liposome. While not the preferred embodiment of this invention, the derivatives of natural sialic acid shown above may also be synthetically attached via a non-hydrolyzable bond by removing the acetyl group in examples #1–4 or the glycol group in example #5. The net effect of this removal is to expose a primary amino group which can be derivatized with succinimedyl acetyl thio acetic acid to form an amide linkage (—CONH—) which is a bond that cannot be hydrolyzed by a circulating indogenous enzyme such as neuraminidan. This new series of synthetically-manipulated neuraminic acid derivatives, when attached to liposomes, provide superior masking from the RES.

Figure 2:
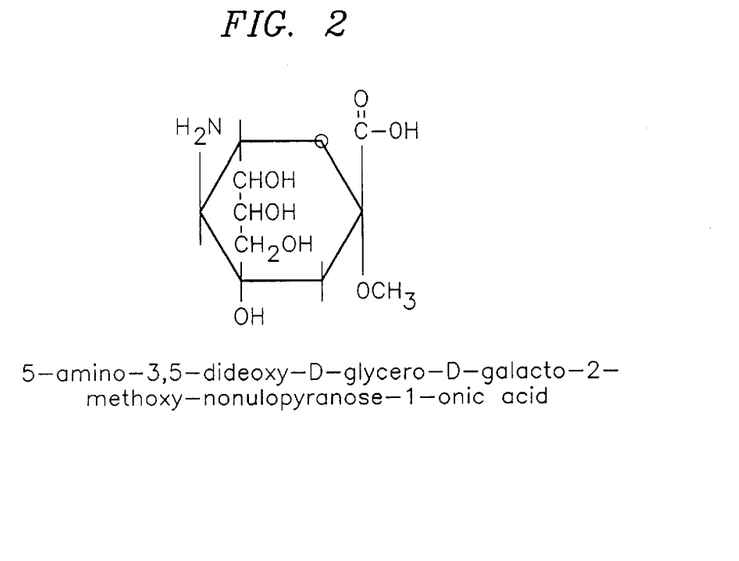
FIG. 2 represents B-methoxyneuraminic acid structure.

The preferred embodiment, however, is the synthetic, B-methoxy form of neuraminic acid shown in FIG. 2.

What is claimed is:

1. A method for the in vivo administration of therapeutic or diagnostic agents, which method comprises:

preparing a formulation comprising;
a first component comprising a liposome carrying one or more diagnostic or therapeutic agents;
a second component attached through a covalent bond to the external surface of said first component comprising neuraminic acid or a derivative thereof that prevents recognition of the liposome by the reticuloendothelial system and which cannot be cleaved from the liposome by the action of endogenous enzymes;
and a third component attached through a covalent bond to the external surface of said first component comprising a molecule that binds the liposome to a specific site in the body, other than RES tissue;
and delivering said formulation to a subject.

2. The method according to claim 1 further comprising a bridging molecule in the liposomal membrane with a functional group available for binding said second component to the external surface of the liposome.

3. The method according to claim 1 wherein the third component comprises a monoclonal antibody.

4. A method for internal administration in the therapeutic or diagnostic treatment of a warm-blooded animal comprising preparing a formulation comprising:
a first component which comprises liposomes carrving one or more diagnostic or therapeutic agents; and
a second component comprising a neuraminic acid molecule attached to the liposome wall, said neuraminic acid selected from the group consisting of neuraminic acid with a methoxy group on carbon 2, neuraminic acid with an N-acetyl group attached to the nitrogen on carbon 5, neuraminic acid with N-acetyl groups attached to the nitrogen on carbon 5 and to the oxygen on carbon 9, neuraminic acid with an N-acetyl group attached to the nitrogen on carbon 5 and a lactyl group attached to the oxygen on carbon 9, or neuraminic acid with an N-acetyl group attached to the nitrogen on carbon 5 and an N-glycolyl group attached to the oxygen on carbon 9, that prevents phagocytosis of the liposome by the body's reticuloendothelial system and which cannot be cleaved from the liposome by the body's endogenous enzymes;
and delivering the formulation to the warm blooded animal.

* * * * *